United States Patent [19]
Di Mino et al.

[11] Patent Number: 5,676,695
[45] Date of Patent: Oct. 14, 1997

[54] CORONA DISCHARGE BEAM THERAPY SYSTEM

[76] Inventors: Alfonso Di Mino, 15 Arcadia Rd.; Andre Di Mino, 159 Glen Rd., both of Woodcliff Lake, N.J. 07675; Vincent Di Mino, 12 Kent Rd., Hillsdale, N.J. 07642

[21] Appl. No.: 635,607

[22] Filed: Apr. 22, 1996

[51] Int. Cl.$^6$ ...................................................... A61N 1/02
[52] U.S. Cl. ............................................ 607/154; 607/150
[58] Field of Search ....................................... 607/145, 150, 607/151, 154, 155; 219/600; 600/13; 336/65, 66, 73, 172, 173, 180, 229; 331/69, 70

[56] References Cited

U.S. PATENT DOCUMENTS

| | | | |
|---|---|---|---|
| 4,119,102 | 10/1978 | LeVeen | 607/154 |
| 4,365,622 | 12/1982 | Harrison | 607/154 |
| 4,545,368 | 10/1985 | Rand et al. | 607/98 |
| 4,667,677 | 5/1987 | Di Mino | 128/419 R |
| 4,887,603 | 12/1989 | Morawetz et al. | 128/422 |
| 5,186,181 | 2/1993 | Franconi et al. | 607/156 |
| 5,249,575 | 10/1993 | Di Mino et al. | 607/150 |
| 5,398,822 | 3/1995 | McCarthy | 211/41 |

FOREIGN PATENT DOCUMENTS 1132960  1/1985  U.S.S.R. .

*Primary Examiner*—Jennifer Bahr
*Assistant Examiner*—David M. Ruddy
*Attorney, Agent, or Firm*—Michael Ebert

[57] ABSTRACT

A corona discharge beam therapy system adapted to project the beam onto the skin surface of a living body overlying a problem region, the beam serving to relieve pain and to obtain other beneficial effects. The system includes an energy-generating unit in which a radio-frequency carrier is overmodulated by a sonic signal to produce periodic bursts of radio-frequency energy whose repetition rate corresponds to the frequency of the signal. The output of the unit is fed to a tank circuit tuned to the carrier frequency and housed within the barrel of a portable applicator gun. Supported within the barrel and coupled to the tank circuit is a discharge electrode whose tip is adjacent the mouth of the barrel whereby a corona discharge beam is projected from the tip. The tank circuit which includes a tank coil and an output coil coupled to the tank coil is formed by a series of Pie sections in spaced relation mounted on an insulating tube having ventilating slots in the spaces between the sections. A motor-driven ventilator fan mounted on one end of the tube blows cooling air therein which is discharged from the slots to prevent overheating of the tank circuit and to maintain the efficiency of the unit even after prolonged operation.

8 Claims, 3 Drawing Sheets

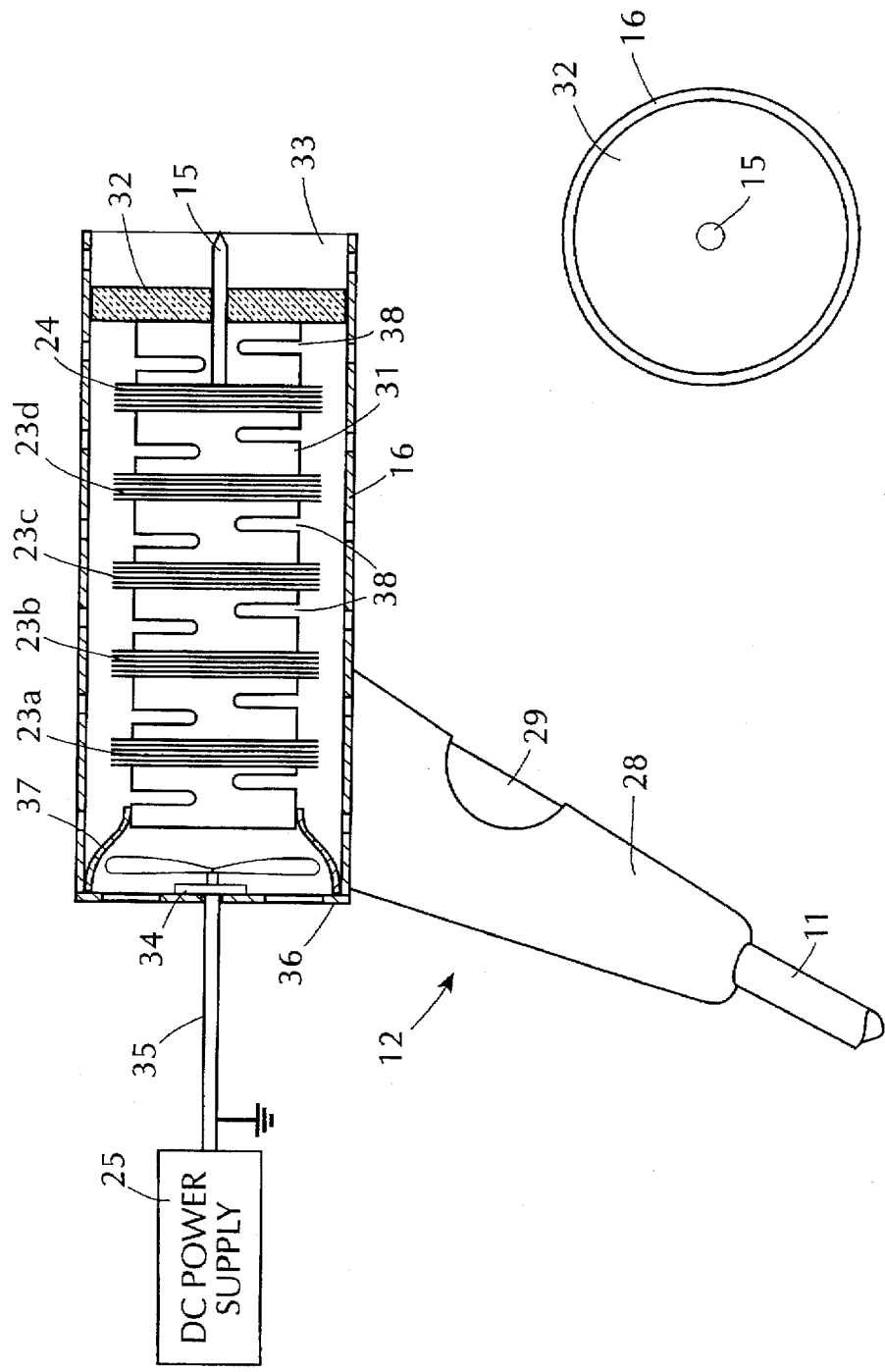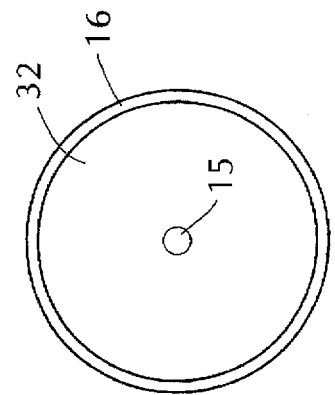

CORONA DISCHARGE BEAM THERAPY SYSTEM

BACKGROUND OF INVENTION

1. Field of Invention

This invention relates generally to a corona discharge therapy system in which the output of a unit producing periodic bursts of radio-frequency energy is applied to a tank circuit connected to a discharge electrode from whose tip a corona discharge beam is projected onto the skin surface of a living body being treated, and more particularly to a tank circuit assembly which is air cooled to prevent the circuit from overheating and to maintain the efficiency of the system.

2. Status of Prior Art

The 1987 Di Mino U.S. Pat. No. 4,667,677 discloses a unit for generating a corona discharge beam and for projecting this beam toward the skin surface of a living body (human or animal) overlying a problem region, the beam serving to relieve pain and to produce other salutary effects. The Di Mino unit includes a radio-frequency carrier generator which is overmodulated with an audio-frequency signal to produce periodic bursts of radio-frequency energy whose repetition rate corresponds to the sonic frequency of the signal. These bursts are stored in a tank circuit coupled to the output of the modulated carrier generator. Connected by a short cable to the output of the tank circuit is a hand-held discharge electrode from which is projected a corona discharge beam, the electrode being manipulated by an operator to scan the skin surface to be treated.

In the system disclosed in 1987 Di Mino U.S. Pat. No. 4,667,677 the hand-held discharge electrode must be in close proximity to the tank circuit included in the energy-generating unit. If the cable extending between the discharge electrode and the tank circuit is long, the resultant loss of energy will be such as to militate against the production of an effective corona discharge beam. As a consequence, the energy-generating unit which includes the tank circuit must be adjacent the patient being treated.

This creates practical difficulties, for if the region to be treated is in the neck or shoulder area, the patient may then have to crouch so as to bring the area of interest next to the discharge electrode. In the 1987 Di Mino patent arrangement, because the cable between the unit and the discharge electrode is necessarily short, the operator is not free to orient the electrode with respect to any body site, but must instead position the body site so that it is in close proximity to the electrode.

To overcome this and other drawbacks, the 1993 Di Mino U.S. Pat. No. 5,249,575 discloses a corona discharge beam therapy system in which the output of the energy-generating unit in which a radio-frequency carrier is overmodulated by an audio-frequency signal, is fed by a relatively long flexible coaxial cable to a tank circuit disposed within the barrel of a portable applicator gun. Supported within the barrel and coupled to the tank circuit is a discharge electrode whose tip lies adjacent the mouth of the barrel. When an operator holding the grip of the gun actuates a trigger switch operatively coupled to the unit, the unit is then turned on to cause a corona discharge beam to be projected from the tip of the electrode toward a selected skin area on the living body being treated.

One major advantage of the 1993 Di Mino system over the 1987 Di Mino system is that the operator who manipulates the gun containing the tank circuit has far greater freedom of movement. Hence the operator can direct the barrel of the gun to project the corona discharge beam to any skin area of the patient regardless of its location.

A problem encountered with the 1993 Di Mino system is that there are many occasions when the system is in prolonged use. As a result of such operation, the tank circuit becomes excessively hot with a consequent reduction in the efficiency of the system. When the tank coil is exactly tuned so that it is in resonance with the operating frequency of the radio-frequency carrier generator, it then draws the least amount of current from the unit and the corona discharge beam is then at its maximum intensity.

The Q or quality factor of a tank circuit consisting of an inductor and a capacitor, both of which are reactive elements, is equal to the ratio of either element to the resistance in the tank circuit. Hence the higher the internal resistance in the tank circuit, the lower its Q. With a high Q tank circuit, as indicated by its resonance curve, the current flowing through the coil dips sharply at the resonance frequency and rises steeply on either side of the resonance frequency. But with a low Q tank circuit, the resonance curve does not exhibit a pronounced dip at the resonance frequency.

It has been found that in a system of the type disclosed in the 1993 Di Mino patent, when the system is in prolonged operation, then in the course of such operation the current flowing through the tank circuit produces an IR loss which heats up the tank circuit. The heat accumulated in the course of prolonged operation gives rise to a significant increase in the internal resistance of the tank circuit, with a resultant reduction in Q. As a consequence, the efficiency of the system diminishes and the strength of the corona discharge beam is lessened, thereby impairing the effectiveness of the therapy.

SUMMARY OF INVENTION

In view of the foregoing, the main object of this invention is to provide a corona discharge beam therapy system in which periodic pulses of radio-frequency energy stored in a tank circuit are applied to a discharge electrode from which the corona discharge beam is projected, the tank circuit being so cooled as to prevent it from overheating in the course of prolonged operation whereby the system operates efficiently regardless of the duration of operation.

More particularly, an object of the invention is to provide a tank circuit assembly in which the tank coil and the output coil which constitute the tank circuit are formed by a series of equi-spaced Pie sections mounted on an insulation tube having in the spaces between the sections ventilating slots through which cool air is discharged to cool the sections.

Also an object of the invention is to provide a hand-held applicator gun in a system of the above type, which gun houses in its barrel the tank circuit assembly and the discharge electrode.

Briefly stated, these objects are attained in a corona discharge beam therapy system adapted to project the beam onto the skin surface of a living body overlying a problem region, the beam serving to relieve pain and to obtain other beneficial effects. The system includes an energy-generating unit in which a radio-frequency carrier is overmodulated by a sonic signal to produce periodic bursts of radio-frequency energy whose repetition rate corresponds to the frequency of the signal. The output of the unit is fed to a tank circuit tuned to the carrier frequency and housed within the barrel of a portable applicator gun. Supported within the barrel and coupled to the tank circuit is a discharge electrode whose tip is adjacent the mouth of the barrel whereby a corona discharge beam is projected from the tip.

The tank circuit which includes a tank coil and an output coil coupled to the tank coil is formed by a series of Pie sections in spaced relation mounted on an insulating tube having ventilating slots in the spaces between the sections. A motor-driven ventilator fan mounted on one end of the tube blows cooling air therein which is discharged from the slots to prevent overheating of the tank circuit and to maintain the efficiency of the unit even after prolonged operation.

BRIEF DESCRIPTION OF DRAWING

For a better understanding of the invention as well as other objects and further features thereof, reference is made to the following detailed description to be read in conjunction with the accompanying drawings, wherein:

FIG. 5 is a section taken through the barrel of the gun and the tank circuit assembly and the discharge electrode housed therein; and FIG. 6 is a front view of the gun barrel.

DESCRIPTION OF INVENTION

Figure 1:
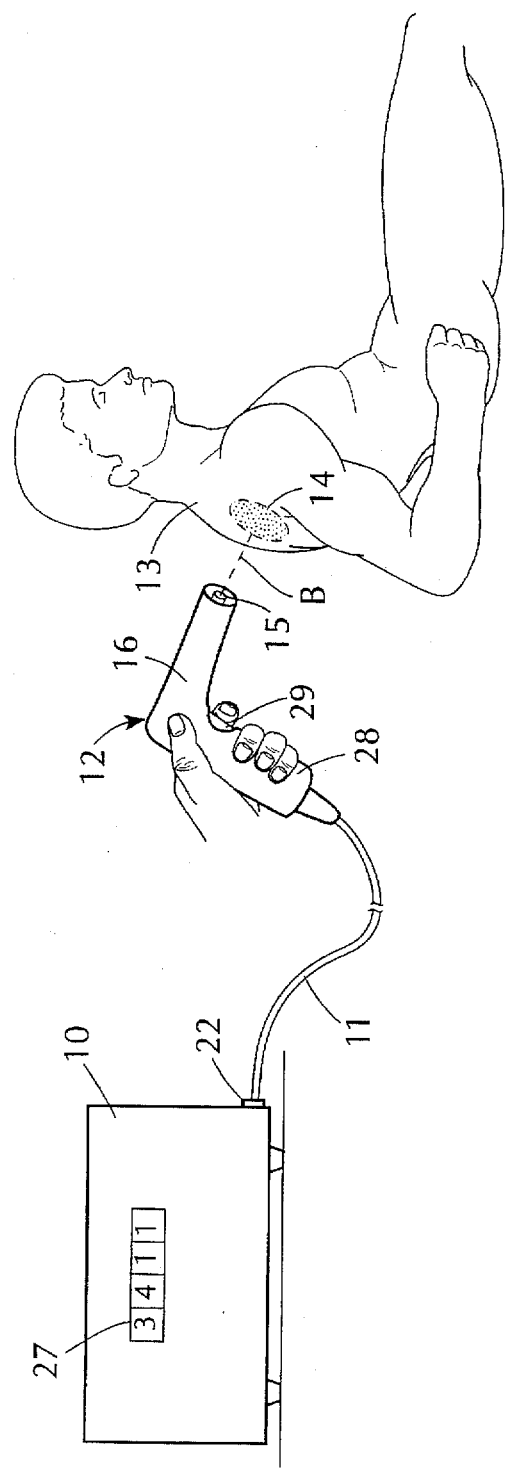
FIG. 1 illustrates the basic components of a corona discharge beam therapy system in accordance with the invention.

The Basic System:

Referring now to FIG. 1, a system in accordance with the invention makes use of an energy-generating unit 10 which yields periodic bursts of radio-frequency energy whose repetition rate is at a sonic frequency. This energy is applied via a relatively long, flexible coaxial cable 11 to a hand-held portable applicator gun 12 within whose barrel 16 is mounted a discharge electrode 15 from which is projected a corona discharge beam B. Beam B is directed toward the skin surface 13 of a patient that overlies a problem region 14 in the body of the patient.

The tip of electrode 15, which is adjacent the mouth of gun barrel 16, is placed within a few centimeters of the skin. The distance between the electrode tip and the skin is such that the clearly visible portion of the corona discharge beam is slightly spaced from the skin, but the less visible portion engages and penetrates the skin. The beam energy is absorbed by the underlying tissue in the problem region 14 of the patient and converted into therapeutic heat and radiation which stimulate a beneficial immune system response. Because of the corona discharge beam, the zone of engagement is small, and in order to irradiate a relatively large skin area, the beam is scanned over this area so that the entire problem region therebelow is subjected to treatment.

A corona discharge is a highly active glow region surrounding a discharge electrode. When the electrode is a pointed wire or metal rod as in the present case, this glow region extends a short distance beyond this point. Assuming the wire is negatively charged, the free electrons in the air in the region of the intense electric field surrounding the wire gains energy in this field to produce positive ions and other electrons by collision. In turn, these new electrons are accelerated and produce further ionization. This cumulative process results in an electron avalanche in which the positive ions are accelerated toward and bombard the charged wire. As a consequence of such ionic bombardment, secondary electrons are ejected from the tip of the electrode which act to sustain the corona discharge.

When the voltage applied to the discharge electrode is elevated to a level exceeding the point at which a stable corona discharge is maintained, the air dielectric then completely breaks down to cause a spark discharge. In order to produce a corona discharge, the peak voltage on the discharge electrode must be relatively high but below the level resulting in a spark discharge.

The continuous application of radio-frequency energy of relatively low power will not result in a corona discharge. But because in the energy-generating unit 10, the continuous radio-frequency carrier is periodically interrupted to produce energy in bursts which shock excite a tank coil included in the tank circuit, the resultant energy surges stored in the tank coil and applied to the electrode coupled thereto have a peak amplitude sufficient to produce a sustained corona discharge beam.

Figure 2:
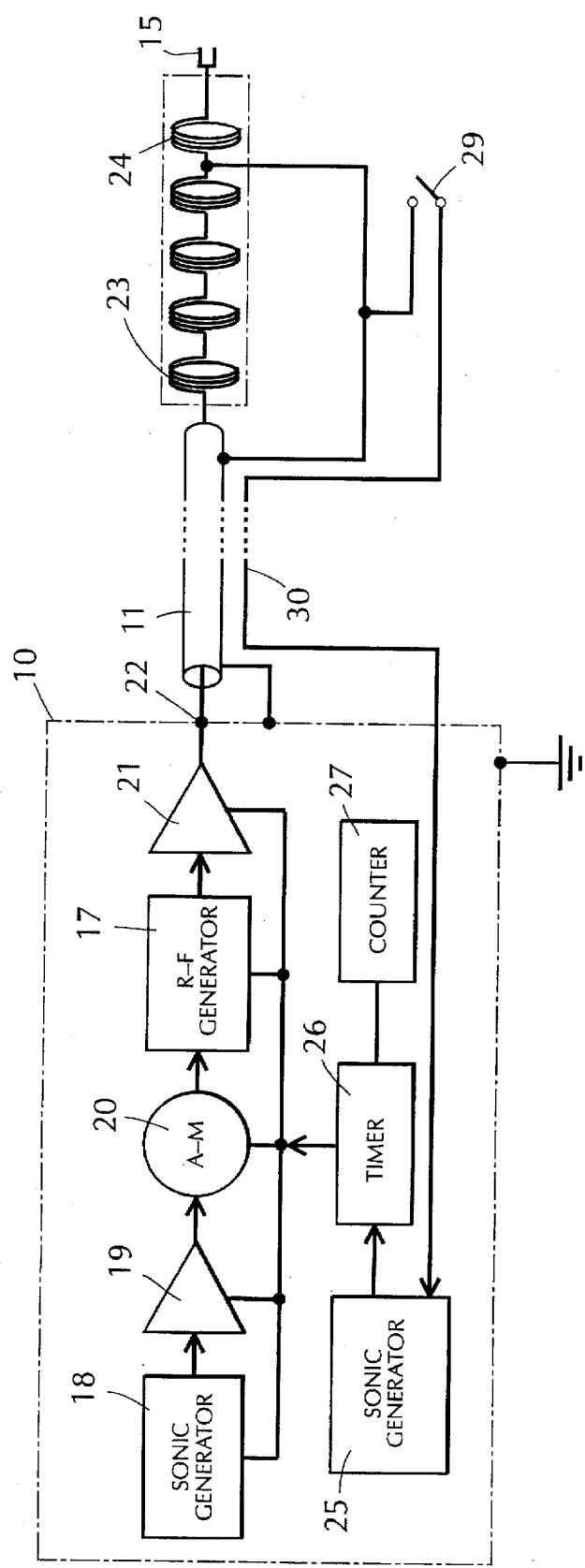
FIG. 2 is a block diagram showing the various stages of the energy-generating unit included in the system and the tank circuit coupled to the output of the unit.

The Energy Generating Unit:

Referring now to FIG. 2, the energy-generating unit 10 includes a radio-frequency generator 17 producing an R-F carrier preferably lying in the low frequency radio range of 200,000 to 450,000 Hz. In practice, this generator is frequency controlled by a piezoelectric crystal oscillator operating, at say, 200 KHz, the carrier generator also being stabilized as to amplitude. A conventional transistorized radio-frequency generator may be used for this purpose.

Also included in the unit is an audio-frequency generator 18 operating in the audio-frequency range of 500 to 5000 Hz to produce a sonic signal. This signal is amplified in amplifier 19 and applied to an amplitude modulator 20, which is so connected to radio-frequency generator 17 as to effect amplitude modulation of the R-F carrier. Audio-frequency generator 18 is preferably a shielded, solid-state, transistorized oscillator.

In amplitude-modulation, the amplitude of the radio-frequency carrier is varied in accordance with the signal, the resultant modulated wave contains side bands that are the sum and difference of the carrier and signal frequencies. If the modulation index "M" is zero, no signal information is conveyed to the carrier. When, however, M=1 (100% modulation), then in the case of a sinusoidal carrier wave, the envelope of the carrier varies from zero to twice the value of its unmodulated amplitude. But if "M" exceeds unity, the carrier is then overmodulated, and as a consequence the carrier is periodically interrupted at a repetition rate in accordance with the audio-frequency signal.

Figure 3:
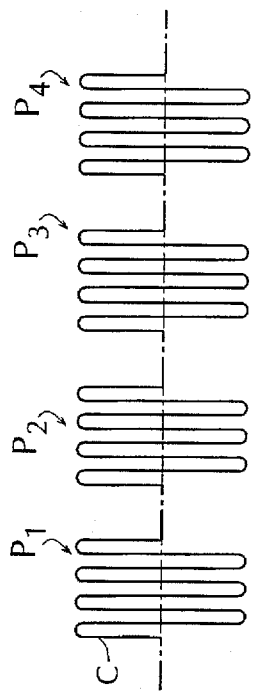
FIG. 3 illustrates the waveform of the bursts of radio-frequency energy produced in the energy-generating unit.

In the present invention, as shown in FIG. 3, the radio frequency carrier C is overmodulated by the sonic frequency signal, thereby giving rise to periodic bursts $P_1$, $P_2$, $P_3$, etc. of radio-frequency energy whose repetition rate is at the sonic frequency. These bursts of energy from R-F generator 17 are applied through an output amplifier 21 to the output jack 22 of the energy-generator unit 10.

Plugged into output jack 22 of the energy generating unit 10 is one end of coaxial cable 11 which connects the output of the unit to the multi-section tank coil 23 of a tank circuit, the tank circuit is housed within the barrel 16 of the applicator gun, and its tank coil 23 is tuned to the carrier frequency of the unit. Tank coil 23 is inductively coupled to an output coil 24 to which is connected the discharge electrode 15.

It is to be noted that the outer shielding conductor of the coaxial cable 11 is grounded, the inner conductor connecting one end of the tank coil 23 to output jack 22. The other end of the tank coil and the corresponding end of the output coil are connected to the grounded outer conductor. Because of this arrangement, there is no radiation from coaxial cable 11 and there is no loss of energy even when the cable is long.

Because tank coil 23 is shock excited by the bursts $P_1$, $P_2$, etc. of the radio-frequency energy, the resultant damped wave surges in coil 23 have a high peak amplitude, and this causes the resultant corona discharge to produce a beam which is both visible and audible. The reason it is visible is that the corona beam in the region adjacent the electrode tip produces a blue glow, and the reason it is audible is that the bursts of energy are at a sonic rate and can therefore be heard. In practice, the power output of the system may be in the order of 1 to 100 watts.

We have found that the resultant heat and radiation induced by the corona discharge beam in a painful region of the human body is capable of relieving this pain within a relatively short time. And we have also found that in some instances, a longer exposure of the problem region to the corona discharge beam, in the case of inflammation due to an arthritis condition, will minimize the swelling, and that a marked reduction in swelling will be experienced after several treatments. Treatment with a corona discharge beam system in accordance with the invention has been found to be efficaceous with osteoarthritis, tendenitis, bursitis and various sports injuries, such as epicondylitis (tennis elbow) and carpal tunnel syndrome (repetitive stress syndrome).

Figure 4:
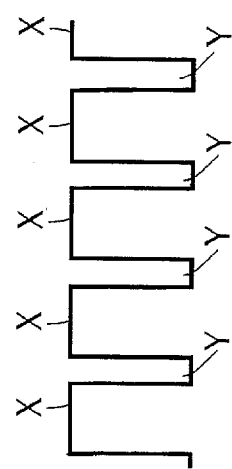
FIG. 4 shows the cyclical wave form produced by the timer included in the unit.

Unit 10 is provided with a direct-current power supply whose output is applied to the stages of a unit through a cycle timer switch 26 so that the unit is activated only when the cycle timer switch is "on." The cycle timer switch operation is such as to cyclically activate the unit for a predetermined time period during which a corona discharge beam is produced, successive cycles being separated by a shorter relaxation interval during which the timer switch is off. As shown by the on-off wave in FIG. 4, each cycle X may have a 15-second "on" duration and each relaxation interval a 3-second "off" duration. In practice, other duty cycles may also be efficacious.

The reason for cyclically activating the unit is that during each inactive interval, the heat produced in the body tissue during the preceding active cycle is permitted to be propagated by heat conduction from the skin surface into the interior of the problem region, thereby reducing the skin temperature and avoiding overheating that may occur should the unit be on continuously for a prolonged period. The cyclical operation of the unit also prevents overheating of the unit itself should the unit be kept on continuously for a prolonged period.

The timer also makes it possible to meter the dosage applied to the patient, this being done by means of a digital counter 27 coupled to the timer. Counter 27, which is resettable, counts the number of timing cycles that occur; hence if each cycle has a 15-second duration, followed by a 3-second off interval, then the counter will count three "on" cycles per minute. If, therefore, the operator is instructed for a given treatment to apply a dosage of 10 cycles to a patient, he can readily do so. And the timer-counter arrangement also makes it possible to bill a patient on the basis of the number of cycles of treatment in terms of treatment units (TU).

Gun 12 is provided with a grip 28 having a trigger switch 29 mounted thereon. This switch, one contact of which is grounded, is connected by a line 30 to power supply 25. In this way, the unit 10 is only turned on when an operator holding the gun 12 in his hand actuates the trigger switch. In practice, the trigger switch may be arranged to actuate a relay having a time delay characteristic, so that once the trigger is momentarily pulled, the unit is turned on for, say, a 15-second interval, and does not release until this interval is completed.

Because the operator is free to manipulate the gun which is connected to unit 10 by a long cable (say 6 feet in length), he is able to treat any region of a human or animal patient. In treating an animal such as a horse, the audio sound produced by the unit when a corona discharge take place may startle the animal and make it difficult to treat the animal.

To avoid startling the animal, the unit may include a sound generator which produces a tone at the same frequency as that produced by the corona discharge beam, but somewhat louder. This sound generator can be switched on by the operator before subjecting the animal to treatment so that the animal becomes accustomed to this sound, and when the corona discharge beam is then turned on, its sound has no effect on the animal.

Tank Circuit Assembly:

It is known to divide a winding into Pie sections for the purpose of reducing the distributed capacitance of the winding. In a tank circuit assembly in accordance with the invention as shown in FIGS. 2 and 5, the tank coil 23 and the output coil 24 which constitute the tank circuit are formed by Pie sections so as to make it possible to cool these coils and prevent their becoming overheated in the course of prolonged operation.

Tank coil 23 is divided into equi-spaced Pie sections 23A, 23B, 23C and 23D which are connected in series. Tank coil 23, as shown in FIG. 2, is connected through cable 11 to the output of unit 10 which supplies to this coil periodic bursts of radio-frequency energy. Output coil 24 is formed by a Pie section which is inductively coupled to tank coil 23 and is spaced therefrom. The Pie sections which constitute the tank circuit are all mounted on an open-ended cylindrical insulating tube 31 of synthetic dielectric material of high strength.

Tube 31 is coaxially disposed within the cylindrical barrel 16 of applicator gun 12. This barrel is formed of open mesh material or otherwise foraminated or apertured to ventilate the barrel. Or the tank circuit asembly may be coaxially mounted within a larger barrel whose inner wall is spaced from the sections to allow for air circulation.

The leading end of tube 31 is closed by a circular insulating wafer 32 mounted adjacent the front end of barrel 16. Extending through a center bore in wafer 32 is the discharge electrode 15 which is connected to output coil 24 of the tank circuit. The tip of electrode 15 which projects forwardly from wafer 32 lies within the open mouth 33 of the barrel 16 so that the corona discharge beam is projected from the mouth of the barrel.

Mounted within the rear end of barrel 16 is a miniature fan 34 driven by a d-c motor connected by a line 35 to the D-C power supply 25 included in unit 10. Fan 34 is supported on the inner wall of an aperture plate 36 enclosing the rear end of barrel 16. Fan 34 is coupled by a shroud 37 to the open rear end of insulating tube 31, so that air drawn from the atmosphere through aperture plate 36 is blown into the tube. Fan 34 is continuously energized and remains energized when the corona-discharge beam system is turned off so that when this system is again turned on the tank circuit is in a cool state.

Insulating tube 31 is provided in the spaces between the Pie sections which form the tank circuit and in the spaces at the front and rear ends of this circuit with an array of ventilating slots 38.

Thus when trigger 29 is pulled by an operator holding in his hand the grip 28 of the applicator gun, to render the system operative, a corona discharge beam is then projected from electrode 15. Fan 37 is then operating to blow cool, air drawn through apertured plate 36 into tube 16 on which is mounted the Pie sections forming the tank circuit. The cool air blown into insulating tube 16 cannot exit from its closed leading end, but can only be discharged from the array of ventilating slots 38. Hence cool air discharged from these slots acts to cool the Pie sections of the tank circuit and to dissipate the heat into the atmosphere.

As a consequence, tank coil 23 and output coil 24 of the tank circuit assembly housed within the barrel of the applicator gun are air cooled in the course of operation of the corona discharge beam system, and the coils are prevented from overheating even when the system is in prolonged operation. When, therefore, the tank coil is tuned to exact resonance with the radio-frequency carrier generated in unit 10, it does not deviate from resonance in the course of prolonged operation, nor does it suffer from a reduction in Q. Hence the efficiency of the system is maintained regardless of the duration of operation.

While there has been shown and described a preferred embodiment of a corona discharge beam system in accordance with the invention, it will be appreciated that many changes and modifications may be made therein without, however, departing from the essential spirit thereof.

We claim:

1. A corona discharge beam therapy system adapted to project the beam onto the surface of a living body overlying a problem region to be treated, said system comprising:

A. an energy-generating unit yielding a radio-frequency carrier that is interrupted at an audio-frequency rate to produce periodic bursts of radio-frequency energy; and B. a tank circuit assembly provided with a tank coil coupled to said unit to store said periodic bursts of energy and an output coil coupled to said tank coil to apply said bursts to a discharge electrode from which said beam is projected, said tank coil and said output coil being formed by spaced Pie sections mounted on an insulating tube having ventilating slots in the spaces between the Pie sections, said assembly including a fan coupled to one end of the tube to blow air therein that is discharged through the slots to said sections to prevent overheating thereof in the course of operation to maintain the efficiency of the system.

2. A system as set forth in claim 1, in which said unit includes a radio-frequency generator to produce said carrier, an audio-frequency generator to produce a sonic signal, and means to overmodulate said carrier with said sonic signal to periodically interrupt the carrier.

3. A system as set forth in claim 2, further including a d-c power supply to power said radio-frequency generator and said audio-frequency generator.

4. A system as set forth in claim 1, in which said assembly is housed in the barrel of an applicator gun whose grip is provided with a trigger switch to turn on said unit.

5. A system as set forth in claim 1, in which the fan is coupled by a shroud to said end of the tube.

6. A system as set forth in claim 5, in which the other end of the tube is closed by an insulating wafer on which the electrode is supported, the electrode being connected to the output coil.

7. A system as set forth in claim 6, in which the tank circuit assembly is mounted in the barrel of an applicator gun and the electrode lies within the mouth of the barrel.

8. A system as set forth in claim 7, in which the barrel is apertured to permit the discharge of cooling air therein.

* * * * *